United States Patent
Park et al.

(10) Patent No.: US 9,573,869 B2
(45) Date of Patent: Feb. 21, 2017

(54) BISPHENOL A PREPARATION APPARATUS AND PREPARATION METHOD

(71) Applicant: LG CHEM, LTD., Seoul (KR)

(72) Inventors: Jong Suh Park, Daejeon (KR); Joon Ho Shin, Daejeon (KR); Tae Woo Kim, Daejeon (KR); Jong Ku Lee, Daejeon (KR); Se Ho Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/904,028

(22) PCT Filed: Jul. 11, 2014

(86) PCT No.: PCT/KR2014/006263
§ 371 (c)(1),
(2) Date: Jan. 8, 2016

(87) PCT Pub. No.: WO2015/005726
PCT Pub. Date: Jan. 15, 2015

(65) Prior Publication Data
US 2016/0159716 A1 Jun. 9, 2016

(30) Foreign Application Priority Data

Jul. 11, 2013 (KR) .................. 10-2013-0081554
Jul. 11, 2013 (KR) .................. 10-2013-0081555

(51) Int. Cl.
| | |
|---|---|
| C07C 37/20 | (2006.01) |
| B01J 19/00 | (2006.01) |
| C07B 63/00 | (2006.01) |
| C07C 37/68 | (2006.01) |
| B01J 19/24 | (2006.01) |
| C07C 37/76 | (2006.01) |
| C07C 37/82 | (2006.01) |
| C07C 37/84 | (2006.01) |
| C07C 37/74 | (2006.01) |

(52) U.S. Cl.
CPC .............. *C07C 37/685* (2013.01); *B01J 19/24* (2013.01); *C07B 63/00* (2013.01); *C07C 37/20* (2013.01); *C07C 37/74* (2013.01); *C07C 37/76* (2013.01); *C07C 37/82* (2013.01); *C07C 37/84* (2013.01); *B01J 2219/00103* (2013.01); *B01J 2219/24* (2013.01)

(58) Field of Classification Search
CPC .......... C07C 37/20; C07C 37/76; C07B 63/00; B01J 19/24
USPC ........................................ 568/724; 422/187
See application file for complete search history.

(56) References Cited

U.S. PATENT DOCUMENTS

2005/0222467 A1   10/2005   Kodama et al.

FOREIGN PATENT DOCUMENTS

| | | |
|---|---|---|
| CN | 1169977 A | 1/1998 |
| CN | 1255112 A | 5/2000 |
| CN | 1358165 A | 7/2002 |
| CN | 1738787 A | 2/2006 |
| CN | 1918097 A | 2/2007 |
| CN | 101626998 A | 1/2010 |
| JP | 5-345737 A | 12/1993 |
| JP | 2005-132798 A | 5/2005 |
| JP | 2005-220094 A | 8/2005 |
| JP | 2007-224020 A | 9/2007 |
| KR | 10-2005-0053531 A | 6/2005 |
| KR | 10-2008-0077104 A | 8/2008 |
| KR | 10-0899496 B1 | 5/2009 |

OTHER PUBLICATIONS

Towler et al., "Utilities and Energy Efficient Design," Chemical Engineering Design, 2nd Edition, Principles, Practice and Economics of Plant and Process Design, pp. 103-160 (pub. Jan. 13, 2012).

*Primary Examiner* — Sikarl Witherspoon
(74) *Attorney, Agent, or Firm* — Dentons US LLP

(57) ABSTRACT

Provided are an apparatus and a method for preparing bisphenol A. In the present invention, all or some of a mother liquid stream is circulated to a flash rector through a bypass line after crystallization in a process of preparing bisphenol A so as to increase a conversion rate of bisphenol A in a reactor, reduce energy, and use a heating source of phenol to be discharged to an upper side of the flash reactor, and thus the reaction efficiency of the whole process can be increased.

18 Claims, 3 Drawing Sheets

BISPHENOL A PREPARATION APPARATUS AND PREPARATION METHOD

This application is a National Stage Application of International Application No. PCT/KR2014/006263, filed on Jul. 11, 2014, which claims the benefit of Korean Patent Application No. 10-2013-0081555, filed on Jul. 11, 2013 and Korean Patent Application No. 10-2013-0081554, filed on Jul. 11, 2013, all of which are hereby incorporated by reference in their entirety for all purposes as if fully set forth herein.

TECHNICAL FIELD

The present invention relates to an apparatus and a method for preparing bisphenol A.

BACKGROUND ART

Bisphenol A is prepared from a reaction of acetone and excessive phenol in the presence of an acidic catalyst. In order to obtain high-purity bisphenol A from this reaction product, low boiling point materials including water is removed, bisphenol A and/or solid adduct crystals of bisphenol A and phenol are precipitated by crystallization, a slurry including the solid adduct is separated into solids and liquids, and phenol is removed from the recovered solid adduct, so that bisphenol A is obtained.

A continuous crystallization process has been industrially used to efficiently purify a large amount of a reactant. In the continuous crystallization process, a slurry including the solid adduct obtained within a crystallizer is separated into solids and liquids, and a solid adduct is recovered and a liquid phase remains. The liquid phase includes phenol in an amount of about 70 wt %, bisphenol A in an amount of about 15 wt %, and other by-products. Thus, in order to reuse phenol included in the liquid phase, a reaction mother liquid from which some by-products are removed is cyclically supplied to a reactor that requires excessive phenol. In this process, it is required to increase the efficiency of the reactor in the above-described reaction.

DISCLOSURE

Patent Document

1. Korean Patent No. 0899496

Technical Problem

The present invention provides an apparatus and a method for preparing bisphenol A.

Technical Solution

The present invention relates to an apparatus for preparing bisphenol A. FIG. 2 is a process diagram illustrating an exemplary apparatus for preparing bisphenol A according to the present invention. In one example, a bisphenol A preparing apparatus may include a reaction unit 10, a reaction product separation unit 20, and a bisphenol A purification unit 30. For example, the reaction unit 10 may include one or more of the group consisting of a feed 1, a main reactor 11, a recovery reactor 12, a reaction product stream 13, and a recovered reaction product stream 14. Further, the reaction product separation unit 20 may include one or more of the group consisting of a dehydrator 21, a co-catalyst processor 22, a flash reactor 23, a reactor reflux stream 28, and a bisphenol A production stream 29. Furthermore, the bisphenol A purification unit 30 may include one or more of the group consisting of a first crystallizer 31, a first solid-liquid separator 32, a second crystallizer 33, a second solid-liquid separator 34, a primary mother liquid stream 35, a primary bisphenol A purification stream 36, a secondary mother liquid stream 37, and a secondary bisphenol A purification stream 38. An exemplary preparing apparatus may include: a main reactor 11 that discharges a reaction product of a reaction between phenol and acetone through a reaction product stream 13; a flash reactor 23 that separates the reaction product stream 13 into a bisphenol A concentration stream 27 and a phenol concentration stream 24; a bisphenol A purification unit 30 that separates the bisphenol A concentration stream 27 into a bisphenol A purification stream 38 and a mother liquid stream 35 and discharges the separated mother liquid stream to the main reactor 11; and a bypass line 15 that introduces at least some of the separated mother liquid stream 35 into the flash reactor 23. In an example, the preparing apparatus may further include a recovery reactor 12 that discharges a recovered reaction product, which is obtained by additionally reacting the mother liquid stream 35 separated in the bisphenol A purification unit 30, to the main reactor 11 through the recovered reaction product stream 14. In this case, the bypass line 15 may be positioned between the recovery reactor 12 and the main reactor 11. In the present specification, the term "recovered reaction product" may mean a reaction product obtained by additionally reacting the separated mother liquid through the recovery reactor 12. In the following descriptions, the recovered reaction product and the mother liquid may be synonymous, and likewise, the recovered reaction product stream and the mother liquid stream may be synonymous. In the above descriptions, a feed 1 including acetone and phenol may be introduced into the main reactor 11, and thus a specific ratio of phenol to acetone to be described later can be adjusted. Further, the reaction product stream 13 passing through the main reactor 11 may be a mixture preferentially including bisphenol A and water in addition to unreacted phenol and acetone. In the present invention, at least some of the mother liquid stream 35 separated in the bisphenol A purification unit 30 is introduced into the flash reactor 23 through the bypass line 15, and thus the reaction efficiency of the main reactor 11 can be improved. If all of the mother liquid stream is discharged to the main reactor, acetone additionally needed for the main reactor 11 may be supplied in consideration of the phenol content in the mother liquid. However, in this case, since the mother liquid includes bisphenol A, a conversion rate of bisphenol A in the main reactor 11 decreases. That is, since the mother liquid includes a large amount of bisphenol A, it is disadvantageous to introduce bisphenol A into the main reactor 11 that produces bisphenol A in terms of the reaction efficiency. Therefore, by introducing the mother liquid into the flash reactor 23 through the bypass line 15, it is possible to increase the reaction efficiency of the entire reactor.

In the present specification, the term "mother liquid stream" refers to a resultant product obtained by removing materials based on bisphenol A from a bisphenol-A-containing component in the bisphenol A purification unit 30, and may refer to, for example, a liquid phase obtained by separating crystallized adduct of bisphenol A and phenol by the solid-liquid separator after crystallization. In the present specification, the mother liquid stream may include the primary mother liquid stream 35 and/or the secondary mother liquid stream 37. In the following descriptions, the term "mother liquid stream" may refer to either the primary mother liquid stream or the secondary mother liquid stream. Furthermore, in the present specification, the crystallized adduct of bisphenol A and phenol separated by the solid-liquid separator may be discharged to the bisphenol A purification stream. In the following descriptions, the primary bisphenol A purification stream 36 and/or the secondary bisphenol A purification stream 38 may be referred to by the term "bisphenol A purification stream."

Stoichiometrically, in production of bisphenol A, 2 M phenol and 1 M acetone are used to produce 1 M bisphenol A with 1 M water. However, industrially, bisphenol A is prepared by reacting acetone with excessive phenol in the presence of an acidic catalyst. In order to obtain high-purity bisphenol A from this reaction product, the reaction product is crystallized, the crystallized adduct of bisphenol A and phenol are precipitated, the thus a crystallized slurry is separated into solids and liquids, and phenol is removed from the recovered crystals. In the acid catalytic reaction of phenol and acetone, a ratio of phenol to acetone may be, for example, 5:1, 7:1, 8:1, or 9:1. Typically, the reaction is continuously carried out, and may be carried out at a temperature of, generally, 45° C. to 110° C., 50° C. to 105° C., 55° C. to 100° C., or 58° C. to 90° C. For example, the acidic catalyst may include strong inorganic acids, homogeneous and heterogeneous acids such as hydrochloric acid or sulfuric acid, or Brønsted or Lewis acids thereof. Further, preferably, a gel-type or sulfonated porous, cross-linked polystyrene resin (acidic ion exchanger) including divinylbenzene as a cross-linking agent may be used. In addition to the catalyst, a thiol may be generally used as a co-catalyst, and for example, methyl mercaptan may be used. As the main reactor 11, for example, a vertical fixed-bed reactor filled with a sulfonic acid type cation exchange resin catalyst may be used, and by supplying a phenol source and an acetone source to this reactor, a reaction can be continuously carried out. After the reaction is carried out for a certain period of time, the operation may be stopped to clean or replace the deteriorated catalyst. In a reaction between phenol and acetone in the presence of an acidic catalyst, a reaction product stream 13 may be formed as a mixture preferentially including bisphenol A and water in addition to unreacted phenol and acetone. Further, typical byproducts of a condensation reaction, such as 2-(4-hydroxyphenyl)-2-(2-hydroxyphenyl)propane (op-BPA), substituted indanes, hydroxyphenyl indanols, hydroxyphenyl chromanes, spiro-bis-indanes, substituted indenols, substituted xanthenes, and more highly condensed compounds having three or more phenyl rings in the molecular structure, may be generated. Furthermore, additional minor components, such as anisole, mesityl oxide, mesitylene and diacetone alcohol, may be formed as a result of self-condensation of acetone and reaction with impurities in the raw materials. Not only secondary products such as water but unreacted materials such as phenol and acetone can adversely affect the suitability of bisphenol A for the production of polymers, and thus may be removed through suitable processes.

In a specific example of the present invention, the preparing apparatus may further include a dehydrator 21 that is positioned between the main reactor 11 and the flash reactor 23 and separates a reaction product stream 13 into a reactor reflux stream 28 and a bisphenol A production stream 29. In an example, the dehydrator 21 may be a distiller capable of removing a low boiling point material. The bisphenol A production stream 29 may be a stream obtained by heating the reaction product stream 13 and removing water in the dehydrator 21. The reaction product stream 13 may be a mixture preferentially including bisphenol A and water in addition to unreacted phenol and acetone. The dehydrator 21 can vaporize and remove materials having lower boiling points than bisphenol A, including water, from the mixture. A temperature at a lower portion within the dehydrator can be adjusted in a range of 150° C. to 200° C., 155° C. to 195° C., 160° C. to 190° C., or 165° C. to 185° C., and a pressure within the dehydrator can be adjusted in a range of 200 mmHg to 760 mmHg, 300 mmHg to 730 mmHg, 400 mmHg to 700 mmHg, or 450 mmHg to 680 mmHg. By adjusting the internal temperature and the internal pressure as described above, it is possible to efficiently remove a low boiling point material having a lower boiling point than phenol and bisphenol A. In order to increase the temperature of the dehydrator, an external heating source may be provided. Generally, the external heating source may be supplied through steam.

In an example, the preparing apparatus may further include a heating source that supplies heat to the flash reactor 23. A method of providing the heating source is not particularly limited. For example, an external heating source may be introduced into the flash reactor 23 by providing an additional heat exchanger. In an example, a circulation line through which some of the bisphenol A concentration stream 27 discharged to a lower side is circulated to the flash reactor 23 may be provided, and a third heat exchanger may be provided at the line so as to supply an external heating source to the flash reactor. The reaction product stream can be supplied to the flash reactor 23 as the bisphenol A production stream 29 discharged to a lower side of the dehydrator 21 without the low boiling point material vaporized in the dehydrator 21, and in the flash reactor 23, phenol can be vaporized and removed. In order to vaporize and remove phenol from the reaction product stream from which water is removed and which is supplied from the dehydrator 21, conventionally, a pressure within the flash reactor 23 is lowered using heat from the reaction product stream from which water is removed and which is discharged from the dehydrator 21 without supplying a separate external heating source. However, when no external heating source as described above is supplied, a temperature within the flash reactor 23 may be outside of a lower limit of a target temperature range, and if the temperature is outside of the lower limit of the target temperature range, heat of phenol vaporized and discharged from the flash reactor 23 is reduced and thus cannot be effectively used in melting of crystallized adduct of bisphenol A and phenol to be described later. Therefore, the preparing apparatus of the present invention may supply an external heating source to the flash reactor 23 through a separate heating source so as to increase a temperature within the flash reactor 23, or adjust an internal pressure while increasing an internal temperature. The internal pressure within the flash reactor 23 may be in a range of 100 mmHg to 700 mmHg, 200 mmHg to 600 mmHg, or 300 mmHg to 500 mmHg, and the internal temperature may be in a range of 100° C. to 180° C., 110° C. to 170° C., 120° C. to 160° C., or 130° C. to 160° C. As described above, by adjusting a target internal pressure or a target internal temperature of the flash reactor 23, it is possible to efficiently vaporize phenol.

Phenol is vaporized in the flash reactor 23 and may be discharged to the phenol concentration stream 24. The phenol concentration stream 24 may be discharged to a phenol storage device 3. Phenol to be stored in the phenol storage device 3 may be discharged to the solid-liquid separators 32 and 34 to serve as phenol for cleaning, or may be circulated to the recovery reactor 12 or the main reactor 11. The preparing apparatus according to the present invention can increase an amount of phenol to be stored in the phenol storage device 3 by supplying the external heating source to the flash reactor 23 as described above, and thus can increase an amount of phenol for cleaning to be circulated in the whole process. In an example, a flow rate of the phenol concentration stream 24 to be discharged from the flash reactor 23 may be in a range of 10 parts by weight/hour to 70 parts by weight/hour, 20 parts by weight/hour to 60 parts by weight/hour, or 30 parts by weight/hour to 50 parts by weight/hour. Further, a phenol content in the phenol concentration stream 24 to be discharged from the flash reactor 23 may be 40% to 80%, 42% to 75%, or 45% to 70% by weight with respect to a phenol content in the bisphenol A production stream 29 to be introduced into the flash reactor. Furthermore, a temperature of the phenol concentration stream 24 to be vaporized and discharged from the flash reactor 23 may be 100° C. to 180° C., 110° C. to 170° C., 120° C. to 160° C., 130° C. to 160° C., 135° C. to 160° C., 140° C. to 160° C., or 145° C. to 160° C. Also, the bisphenol A concentration stream 27 may include bisphenol A at 30 to 80 wt %, phenol at 1 wt % to 60 wt %, and unreacted by-products at 5 to 40 wt %, and may be discharged to a lower side of the flash reactor 23.

In an example, the preparing apparatus of the present invention may further include a co-catalyst processor 22 that processes a co-catalyst in the reactor reflux stream 28 and refluxes its resultant product to the main reactor 11. The co-catalyst processor 22 can reflux an overhead stream discharged from the dehydrator 21 or the flash reactor 23 to the main reactor 11, and the overhead stream may be processed with a co-catalyst and its resultant product may be refluxed to the main reactor 11. In an example, the above-described phenol concentration stream 24 may be introduced into the co-catalyst processor 22 through a phenol stream for a co-catalytic process.

The bisphenol A concentration stream 27 discharged from the flash reactor 23 is a stream obtained by completely or partially removing water, as well as acetone and other highly volatile components such as a co-catalyst, in advance by distillation, and may be introduced into the bisphenol A purification unit 30 for additional processes. The bisphenol A purification unit 30 can discharge a slurry stream in a continuous or semi-continuous manner. In a specific example of the present invention, the bisphenol A purification unit 30 of the preparing apparatus may include: a crystallizer that crystallizes adduct of bisphenol A and phenol in the bisphenol A concentration stream 27; and a solid-liquid separator that separates the crystallized adduct of bisphenol A and phenol from a mother liquid. One each of the crystallizer and the solid-liquid separator is positioned, and crystallization and solid-liquid separation can be carried out once. Also, the crystallization and solid-liquid separation may be carried out twice with a first crystallizer, a first solid-liquid separator, a second crystallizer, and a second solid-liquid separator, and may be carried out, for example, three to five times with three to five crystallizers and three to five solid-liquid separators. Through the above-described process, the bisphenol A concentration stream 27 is cooled and crystallized, and thus the crystallized adduct of bisphenol A and phenol can be obtained. In an example, the crystallizer may be a cooler. That is, in the crystallization process, one or more coolers remove heat from the bisphenol A concentration stream including bisphenol A and phenol in a continuous or semi-continuous manner and cause supersaturation, and thus the crystallized adduct of bisphenol A and phenol can be crystallized. The crystallized adduct of bisphenol A and phenol may be in the form of a slurry. Further, in addition to the coolers, a residence time required for destruction of the supersaturation and crystallization may also be provided to the crystallizer. Generally, the pump can circulate the slurry from the crystallizer through the coolers.

Further, in a specific example of the present invention, the slurry including the crystallized adduct of bisphenol A and phenol can be separated into solids and liquids by the solid-liquid separators 32 and 34. In an example, the solid-liquid separator is not particularly limited as long as it can separate solids and liquids, and a typical device in the art can be used. For example, a rotary filter or a centrifuge may be used.

In an example, the preparing apparatus of the present invention may include a first heat exchanger that exchanges heat between the phenol concentration stream 24 separated in the flash reactor 23 and the bisphenol A purification stream separated in the solid-liquid separator to melt the crystallized adduct of bisphenol A and phenol. The phenol concentration stream 24 separated in the flash reactor 23 may be introduced into the first heat exchanger through a solid-liquid separation phenol stream 26. To be specific, the phenol concentration stream 24 can directly or indirectly exchange heat with the bisphenol A purification stream. For example, the phenol concentration stream 24 can transfer heat to another phenol stream that also melts the crystallized adduct of bisphenol A and phenol. That is, heat is transferred to the other phenol stream that melts the crystallized adduct of bisphenol A and phenol from the phenol concentration stream 24 in the form of a high-temperature steam with no need to add a separate heating source, and the above-described melting process can be carried out by the other phenol stream. In another specific example, as illustrated in FIG. 3, the preparing apparatus of the present invention may include a first heat exchanger 6 that exchanges heat between the phenol concentration stream 24 separated in the flash reactor 23 and the bisphenol A purification stream separated in the second solid-liquid separator 34 to melt the crystallized adduct of bisphenol A and phenol; and a second heat exchanger 7 that exchanges heat between the phenol concentration stream 24 separated in the flash reactor 23 and the bisphenol A purification stream separated in the first solid-liquid separator 32 to melt the crystallized adduct of bisphenol A and phenol. In this case, the phenol concentration stream 24 separated in the flash reactor 23 may also be introduced into the first heat exchanger 6 and the second heat exchanger 7 through the solid-liquid separation phenol stream 26. A bisphenol A purification device 2 to be described later melts the crystallized adduct of bisphenol A and phenol to separate bisphenol A and phenol. Before the melting process, with heat from the phenol concentration stream 24, the crystallized adduct of bisphenol A and phenol are melted through the first heat exchanger 6 and/or the second heat exchanger 7. Thus, the external heating source supplied to the flash reactor 23 can be efficiently used and the entire reactor can increase the efficiency and reduce energy accordingly. In an example, the phenol concentration stream 24 that transfers heat through the heat exchangers can be supplied again to the main reactor 11.

In an example, the preparing apparatus of the present invention may further include the bisphenol A purification device 2 that melts the crystallized adduct of bisphenol A and phenol present in the bisphenol A purification stream to be discharged from the bisphenol A purification unit 30 to separate bisphenol A and phenol.

Further, the preparing apparatus of the present invention may further include a mother liquid purification device 4 that removes pentane from the mother liquid streams 35 and 37 separated in the bisphenol A purification unit 30. In the above descriptions, the mother liquid streams 35 and 37 include low boiling point alkane hydrocarbons having 4 to 6 carbon atoms, for example, pentane, in an amount of 5 to 15 wt %, and thus it is possible to vaporize and remove pentane in the mother liquid purification device. The mother liquid to be discharged from the mother liquid purification device 4 may include phenol of 65 wt % to 80 wt %, bisphenol A of 10 wt % to 20 wt %, and other unreacted by-products.

The present invention also relates to a method for preparing bisphenol A. The preparing method may include preparing bisphenol A using the above-described bisphenol A preparing apparatus. An exemplary preparing method may include a step of reacting phenol with acetone in a main reactor 11 and discharging a reaction product through a reaction product stream 13; a step of separating the reaction product stream 13 into a bisphenol A concentration stream and a phenol concentration stream in a flash reactor 23; a step of separating the bisphenol A concentration stream 27 into a bisphenol A purification stream and a mother liquid stream in a bisphenol A purification unit 30 and discharging the separated mother liquid stream 35 to the main reactor 11; and a step of introducing at least some of the separated mother liquid stream 35 into the flash reactor 23 through a bypass line 15. Further, the preparing method may further include a step of supplying heat to the flash reactor 23 through a heating source. Furthermore, in a specific example of the present invention, the preparing method may include additionally reacting the mother liquid stream 35 separated in the bisphenol A purification unit 30 through a recovery reactor 12, discharging a mother liquid to the main reactor through a recovered reaction product stream, and introducing at least some of the mother liquid from the recovered reaction product stream to the flash reactor through the bypass line. In the above descriptions, a feed 1 including acetone and phenol may be introduced into the main reactor 11, and thus the above-described specific ratio of phenol to acetone can be adjusted. In the present invention, since at least some of the mother liquid is introduce into the flash reactor 23 through the bypass line 15, the reaction efficiency of the main reactor 11 can be increased.

In an example, the step of introducing the separated mother liquid stream into the flash reactor through a bypass line in the preparing method may include introducing the separated mother liquid stream at 10% to 100% by weight into the flash reactor. That is, the mother liquid stream to be introduced into the flash reactor 23 through the bypass line 15 may be 10% to 100% by weight of the mother liquid stream separated in the bisphenol A purification unit 30. To be specific, a percentage of the mother liquid stream may be 10% to 100%, 13% to 100%, 15% to 100%, 17% to 100%, 20% to 100%, 22% to 100%, or 25% to 100% by weight. By controlling a ratio of the mother liquid stream to be introduced into the main reactor to the mother liquid stream to be discharged through the bypass line as described above, the reaction efficiency of the main reactor 11 can be increased.

In a specific example of the present invention, the preparing method may further include a step of separating the reaction product stream into a reactor reflux stream 28 and a bisphenol A production stream 29 through a dehydrator 21 positioned between the main reactor 11 and the flash reactor 23. Further, the preparing method of the present invention may further include a step of processing a co-catalyst in the reactor reflux stream 28 and refluxing its resultant product to the main reactor 11 through the co-catalyst processor 22.

Furthermore, in the preparing method of the present invention, the step of separating the bisphenol A concentration stream into a bisphenol A purification stream and a mother liquid stream in a bisphenol A purification unit may include: a step of crystallizing adduct of bisphenol A and phenol in the bisphenol A concentration stream through a crystallizer; and a step of separating the crystallized adduct of bisphenol A and phenol from a mother liquid through a solid-liquid separator. With one each of the crystallizer and the solid-liquid separator, crystallization step and the solid-liquid separation step can be carried out once. Also, the crystallization step and the solid-liquid separation step may be carried out twice with a first crystallizer, a first solid-liquid separator, a second crystallizer, and a second solid-liquid separator, and may be carried out, for example, three to five times with three to five crystallizers and three to five solid-liquid separators. In an example, in the preparing method of the present invention, the step of separating the bisphenol A concentration stream into a bisphenol A purification stream and a mother liquid stream in a bisphenol A purification unit may include: a step of crystallizing adduct of bisphenol A and phenol in the bisphenol A concentration stream through a first crystallizer 31; a step of separating the crystallized adduct of bisphenol A and phenol to be discharged from the first crystallizer 31 from a mother liquid through a first solid-liquid separator 32; a step of recrystallizing the crystallized adduct of bisphenol A and phenol separated in the first solid-liquid separator 32 through a second crystallizer 33; and a step of separating the crystallized adduct of bisphenol A and phenol to be discharged from the second crystallizer 33 from the mother liquid through the second solid-liquid separator 34.

In an example, the preparing method may include a step of exchanging heat between the phenol concentration stream 24 separated in the flash reactor 23 and the bisphenol A purification stream separated in the solid-liquid separator through a first heat exchanger to melt the crystallized adduct of bisphenol A and phenol. Further, in a specific example of the present invention, the preparing method may include a step of exchanging heat between the phenol concentration stream 24 separated in the flash reactor 23 and the bisphenol A purification stream separated in the second solid-liquid separator 34 through a first heat exchanger 6 to melt the crystallized adduct of bisphenol A and phenol; and a step of exchanging heat between the phenol concentration stream 24 separated in the flash reactor 23 and the bisphenol A purification stream separated in the first solid-liquid separator 32 through a second heat exchanger 7 to melt the crystallized adduct of bisphenol A and phenol. The above-described bisphenol A purification device can melt the crystallized adduct of bisphenol A and phenol to separate bisphenol A and phenol, and before the melting process, with heat from the phenol concentration stream 24, the crystallized adduct of bisphenol A and phenol are directly or indirectly melted through the first heat exchanger 6 and/or the second heat exchanger 7, and thus an external heating source supplied to the flash reactor 23 can be efficiently used and the entire reactor can increase the efficiency and reduce energy accordingly.

Further, the preparing method of the present invention may further include a step of melting the crystallized adduct of bisphenol A and phenol present in the bisphenol A purification stream to be discharged from the bisphenol A purification unit 30 to separate bisphenol A and phenol. Through the above-described step, the preparing method of the present invention can be used to separate bisphenol A and phenol in the bisphenol A purification device 2 and ultimately produce bisphenol A.

Advantageous Effects

The present invention circulates all or some of a mother liquid stream to a flash rector through a bypass line after crystallization in a process of purifying bisphenol A so as to increase a conversion rate of bisphenol A in a reactor, reduce energy, and use a heating source of phenol to be discharged to an upper side of the flash reactor, and thus the reaction efficiency of the whole process can be increased.

EXPLANATION OF CODES

Figure 1:
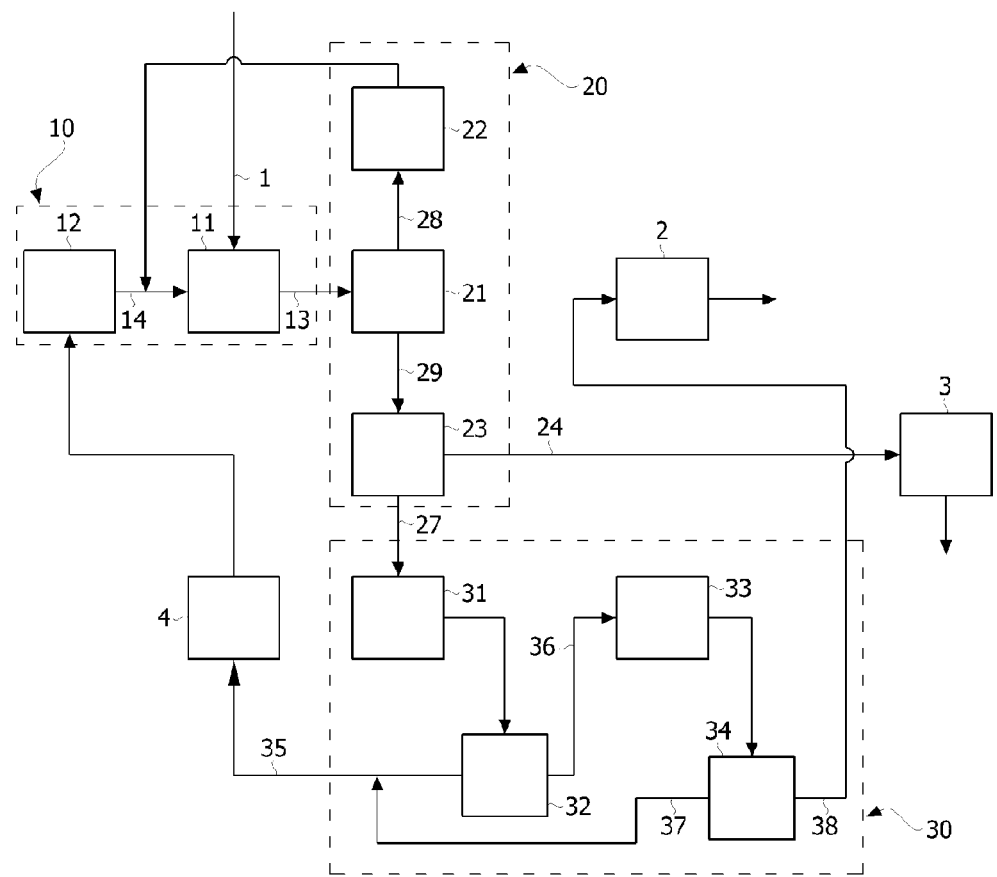
FIG. 1 is a process diagram illustrating a conventional apparatus for preparing bisphenol A.

1: Feed
2: Bisphenol A purification device
3: Phenol storage device
4: Mother liquid purification device
6: First heat exchanger
7: Second heat exchanger
10: Reaction unit
20: Reaction product separation unit
30: Bisphenol A purification unit
11: Main reactor
12: Recovery reactor
13: Reaction product stream
14: Recovered reaction product stream
15: Bypass line
21: Dehydrator
22: Co-catalyst processor
23: Flash reactor
24: Phenol concentration stream
26: Solid-liquid separation phenol stream
27: Bisphenol A concentration stream
28: Reactor reflux stream
29: Bisphenol A production stream
31: First crystallizer
32: First solid-liquid separator
33: Second crystallizer
34: Second solid-liquid separator
35: Primary mother liquid stream
36: Primary bisphenol A purification stream
37: Secondary mother liquid stream
38: Secondary bisphenol A purification stream

MODES OF THE INVENTION

Hereinafter, the above-described bisphenol A preparing apparatus and method will be explained in detail with reference to Examples. However, the scope of the preparing apparatus and method is not limited to the following Examples.

Example 1

Figure 2:
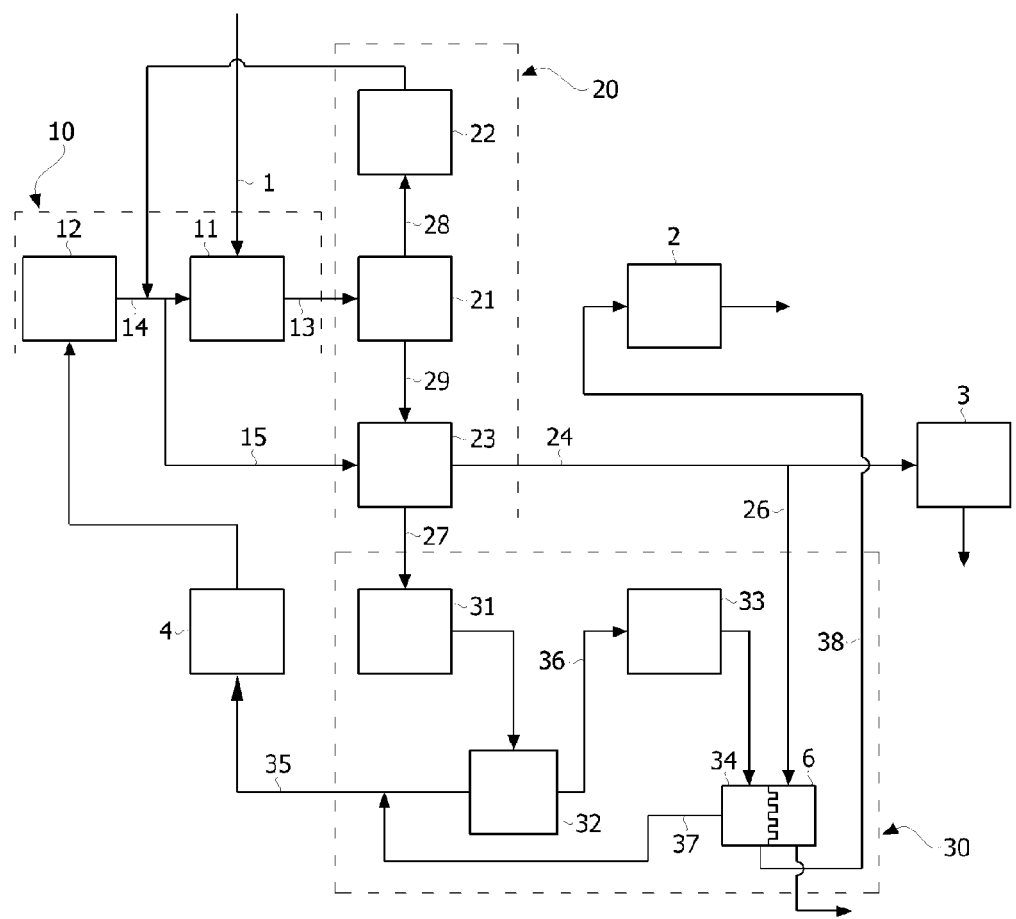
FIG. 2 and FIG. 3 are process diagrams illustrating an apparatus for preparing bisphenol A according to the present invention.
Figure 3:
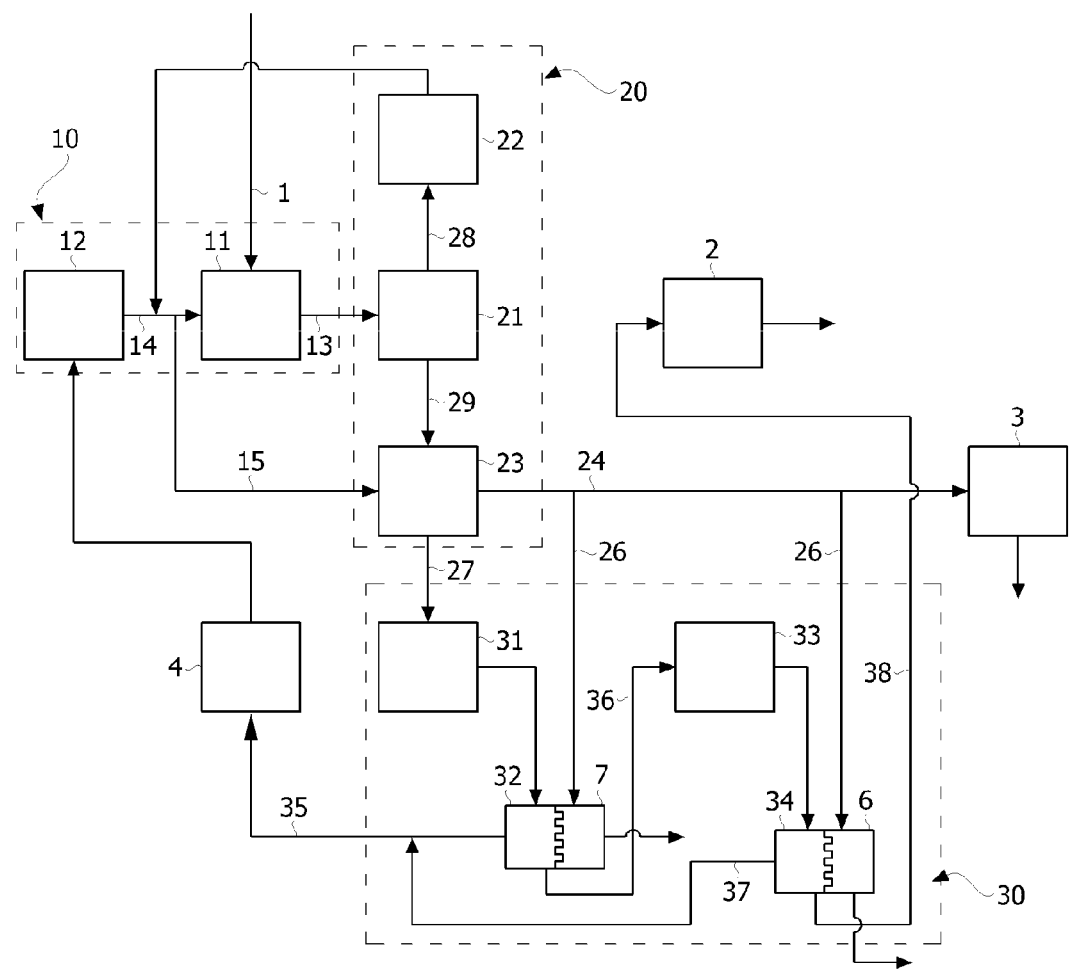

Bisphenol A was prepared using a preparing apparatus and a process as illustrated in FIG. 2. Phenol and acetone were put into a main reactor at a weight ratio of 9:1 and reacted therein at 60° C., and then water was vaporized and removed from a reaction product in a dehydrator at 178° C. and 550 mmHg. The reaction product from which water was removed was supplied to a flash reactor. In the flash reactor, an internal temperature was adjusted to 155° C. and an internal pressure was adjusted to 250 mmHg to vaporize and remove phenol while a separate external heating source was supplied to the flash reactor. A bisphenol A concentration stream without the phenol vaporized in the flash reactor formed a slurry including crystallized adduct of bisphenol A and phenol in a first crystallizer and the slurry supplied to a rotary centrifuge serving as a solid-liquid separator. A liquid phase separated in the rotary centrifuge was supplied to a depentanizer serving as a mother liquid purification device to vaporize and remove pentane, and thus a reaction mother liquid from which pentane was removed was obtained. The crystallized adduct of bisphenol A and phenol separated in the rotary centrifuge was supplied to a bisphenol A purification device through a heat exchanger, and bisphenol A was produced through the bisphenol A purification device. An amount of steam to be used as a heating source in the rotary centrifuge could be reduced.

In the reaction mother liquid, a phenol content was 74 wt %, a bisphenol A content was 16 wt %, and the rest was acetone and other by-products.

As an initial feed, phenol of 24.8 parts by weight/hour and acetone of 4.5 parts by weight/hour were supplied to the main reactor, and thus a reaction liquid of 70 parts by weight/hour was prepared. Water and phenol were removed. Then, crystallization was carried out, and a mother liquid of 57.4 parts by weight/hour was produced. The reaction mother liquid in an amount of 25 wt % was circulated to the flash reactor and mixed in the flash reactor with a stream from a lower side of the dehydrator so as to vaporize phenol of 35.7 parts by weight/hour. After crystallization, the mixture of phenol and bisphenol A was additionally purified, and bisphenol A of 17.1 parts by weight/hour was prepared.

Example 2

Bisphenol A was prepared in the same manner as Example 1 except that the reaction mother liquid in an amount of 50 wt % was circulated to the flash reactor and the rest was put into the main reactor.

Example 3

Bisphenol A was prepared in the same manner as Example 1 except that the reaction mother liquid in an amount of 100 wt % was circulated to the flash reactor and the rest was put into the main reactor.

Comparative Example 1

Bisphenol A was prepared using a preparing apparatus and a process as illustrated in FIG. 1. Phenol and acetone were put into a main reactor at a weight ratio of 9:1 and reacted therein at 60° C., and then water was vaporized and removed from a reaction product in a dehydrator at 178° C. and 550 mmHg. The reaction product from which water was removed was supplied to a flash reactor. In the flash reactor, an internal temperature was adjusted to 155° C. and an internal pressure was adjusted to 250 mmHg to vaporize and remove phenol without supplying a separate external heating source to the flash reactor. A bisphenol A concentration stream without the phenol vaporized in the flash reactor formed a slurry including crystallized adduct of bisphenol A and phenol in a first crystallizer and the slurry supplied to a rotary centrifuge serving as a solid-liquid separator. A liquid phase separated in the rotary centrifuge was supplied to a depentanizer serving as a mother liquid purification device to vaporize and remove pentane, and thus a reaction mother liquid from which pentane was removed was obtained. The crystallized adduct of bisphenol A and phenol separated in the rotary centrifuge was supplied to a bisphenol A purification device after being melted since steam was supplied as a separate external heating source to two rotary centrifuges, and bisphenol A was produced through the bisphenol A purification device.

In the reaction mother liquid, a phenol content was 74 wt %, a bisphenol A content was 16 wt %, and the rest was acetone and other by-products.

As an initial feed, phenol of 24.8 parts by weight/hour and acetone of 4.5 parts by weight/hour were supplied to the main reactor, and thus a reaction liquid of 83 parts by weight/hour was prepared. Water and phenol were removed. Then, crystallization was carried out, and a circulation mother liquid of 56.7 parts by weight/hour was produced. All of this mother liquid was put into the main reactor. After dehydration in the flash reactor, phenol of 34.7 parts by weight/hour in the mother liquid was vaporized. After crystallization, the mixture of phenol and bisphenol A was additionally purified, and bisphenol A of 16.8 parts by weight/hour was prepared.

TABLE 1

|  | Bisphenol A conversion rate (%) | Bisphenol A production amount (parts by weight/hour) | Steam consumption (parts by weight/hour) |
| --- | --- | --- | --- |
| Example 1 | 91 | 17.1 | 43 |
| Example 2 | 93 | 17.3 | 41 |
| Example 3 | 95 | 17.7 | 37 |
| Comparative Example 1 | 90 | 16.8 | 45 |

In Table 1, the conversion rate of bisphenol A was calculated based on an amount of acetone input, and the bisphenol A production amount was calculated based on a bisphenol A production amount of Aspen. Further, the steam consumption was obtained by measuring a flow rate of steam to be introduced into the flash reactor (Examples 1 to 3) or steam to be introduced into the first and second solid-liquid separators (Comparative Example 1). It can be seen from Table 1 that Comparative Example 1 without using a bypass line had a low bisphenol A conversion rate and a low bisphenol A production amount. Further, it can be seen that as a ratio of a reaction mother liquid introduced into a flash reactor through a bypass line increases, the bisphenol A conversion rate is high, the bisphenol A production amount is high, and the steam consumption can be reduced. Furthermore, it can be seen that in Comparative Example 1 in which steam was separately supplied to each solid-liquid separator, the steam consumption is higher than Examples 1 to 3 in which an external heating source was supplied to a flash reactor and crystallized adduct of bisphenol A and phenol to be discharged to a solid-liquid separator were melted with heat from an overhead phenol concentration stream of the flash reactor. Thus, it is confirmed that the preparing apparatus of Examples can reduce energy consumption.

The invention claimed is:
1. A bisphenol A preparing apparatus comprising:
   a main reactor that discharges a reaction product of a reaction between phenol and acetone through a reaction product stream;
   a flash reactor that separates the reaction product stream into a bisphenol A concentration stream and a phenol concentration stream;
   a bisphenol A purification unit that separates the bisphenol A concentration stream into a bisphenol A purification stream and a mother liquid stream and discharges the separated mother liquid stream;
   a recovery reactor that discharges a recovered reaction product, which is obtained by additionally reacting the mother liquid stream separated in the bisphenol A purification unit, to the main reactor through a recovered reaction product stream; and
   a bypass line that is positioned between the recovery reactor and the main reactor and that introduces at least some of the separated mother liquid stream into the flash reactor.

2. The bisphenol A preparing apparatus of claim 1, further comprising:
   a heating source that supplies heat to the flash reactor.

3. The bisphenol A preparing apparatus of claim 1, further comprising:
   a dehydrator that is positioned between the main reactor and the flash reactor and separates the reaction product stream into a reactor reflux stream and a bisphenol A production stream.

4. The bisphenol A preparing apparatus of claim 1, wherein the bisphenol A purification unit comprises:
   a crystallizer that crystallizes adduct of bisphenol A and phenol in the bisphenol A concentration stream; and
   a solid-liquid separator that separates the crystallized adduct of bisphenol A and phenol from a mother liquid.

5. The bisphenol A preparing apparatus of claim 4, wherein the bisphenol A purification unit comprises:
   a first crystallizer that crystallizes adduct of bisphenol A and phenol in the bisphenol A concentration stream;
   a first solid-liquid separator that separates the crystallized adduct of bisphenol A and phenol to be discharged from the first crystallizer from the mother liquid;
   a second crystallizer that recrystallizes the crystallized adduct of bisphenol A and phenol separated in the first solid-liquid separator; and
   a second solid-liquid separator that separates the crystallized adduct of bisphenol A and phenol to be discharged from the second crystallizer from the mother liquid.

6. The bisphenol A preparing apparatus of claim 1, further comprising:
   a bisphenol A purification device that melts crystallized adduct of bisphenol A and phenol present in the bisphenol A purification stream to be discharged from the bisphenol A purification unit to separate bisphenol A and phenol.

7. The bisphenol A preparing apparatus of claim 1, further comprising:
   a mother liquid purification device that removes pentane from the mother liquid stream separated in the bisphenol A purification unit.

8. The bisphenol A preparing apparatus of claim 5, further comprising:
   a first heat exchanger that exchanges heat between the phenol concentration stream separated in the flash reactor and the bisphenol A purification stream separated in the solid-liquid separator to melt the crystallized adduct of bisphenol A and phenol.

9. The bisphenol A preparing apparatus of claim 5, further comprising:
- a first heat exchanger that exchanges heat between the phenol concentration stream separated in the flash reactor and the bisphenol A purification stream separated in the second solid-liquid separator to melt the crystallized adduct of bisphenol A and phenol; and
- a second heat exchanger that exchanges heat between the phenol concentration stream separated in the flash reactor and the bisphenol A purification stream separated in the first solid-liquid separator to melt the crystallized adduct of bisphenol A and phenol.

10. A bisphenol A preparing method comprising:
- a step of reacting phenol with acetone in a main reactor and discharging a reaction product through a reaction product stream;
- a step of separating the reaction product stream into a bisphenol A concentration stream and a phenol concentration stream in a flash reactor;
- a step of separating the bisphenol A concentration stream into a bisphenol A purification stream and a mother liquid stream in a bisphenol A purification unit and discharging the separated mother liquid stream;
- a step of additionally reacting the separated mother liquid stream through a recovery reactor after the mother liquid stream separated in the bisphenol A purification unit, and discharging the separated mother liquid stream to the main reactor through a recovered reaction product stream; and
- a step of introducing at least some of the separated mother liquid stream from the recovered reaction product stream into the flash reactor through a bypass line.

11. The bisphenol A preparing method of claim 10, further comprising:
- a step of supplying heat to the flash reactor through a heating source.

12. The bisphenol A preparing method of claim 10, further comprising:
- a step of separating the reaction product stream into a reactor reflux stream and a bisphenol A production stream through a dehydrator positioned between the main reactor and the flash reactor.

13. The bisphenol A preparing method of claim 10, wherein the step of separating the bisphenol A concentration stream into a bisphenol A purification stream and a mother liquid stream in a bisphenol A purification unit comprises:
- a step of crystallizing adduct of bisphenol A and phenol in the bisphenol A concentration stream through a crystallizer; and
- a step of separating the crystallized adduct of bisphenol A and phenol from a mother liquid through a solid-liquid separator.

14. The bisphenol A preparing method of claim 13, wherein the step of separating the bisphenol A concentration stream into a bisphenol A purification stream and a mother liquid stream in a bisphenol A purification unit comprises:
- a step of crystallizing adduct of bisphenol A and phenol in the bisphenol A concentration stream through a first crystallizer;
- a step of separating the crystallized adduct of bisphenol A and phenol to be discharged from the first crystallizer from a mother liquid through a first solid-liquid separator;
- a step of recrystallizing the crystallized adduct of bisphenol A and phenol separated in the first solid-liquid separator through a second crystallizer; and
- a step of separating the crystallized adduct of bisphenol A and phenol to be discharged from the second crystallizer from the mother liquid through the second solid-liquid separator.

15. The bisphenol A preparing method of claim 10, further comprising:
- a step of melting crystallized adduct of bisphenol A and phenol present in the bisphenol A purification stream to be discharged from the bisphenol A purification unit to separate bisphenol A and phenol.

16. The bisphenol A preparing method of claim 13, further comprising:
- a step of exchanging heat between the phenol concentration stream separated in the flash reactor and the bisphenol A purification stream separated in the solid-liquid separator through a first heat exchanger to melt the crystallized adduct of bisphenol A and phenol.

17. The bisphenol A preparing method of claim 14, further comprising:
- a step of exchanging heat between the phenol concentration stream separated in the flash reactor and the bisphenol A purification stream separated in the second solid-liquid separator through a first heat exchanger to melt the crystallized adduct of bisphenol A and phenol; and
- a step of exchanging heat between the phenol concentration stream separated in the flash reactor and the bisphenol A purification stream separated in the first solid-liquid separator through a second heat exchanger to melt the crystallized adduct of bisphenol A and phenol.

18. The bisphenol A preparing method of claim 10, wherein the step of introducing the separated mother liquid stream into the flash reactor through a bypass line comprises introducing the separated mother liquid stream of 10% to 100% by weight into the flash reactor.

* * * * *